US006893464B2

(12) United States Patent
Kiester

(10) Patent No.: US 6,893,464 B2
(45) Date of Patent: May 17, 2005

(54) METHOD AND APPARATUS FOR PROVIDING AN EXPANDABLE SPINAL FUSION CAGE

(75) Inventor: P. Douglas Kiester, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/091,937

(22) Filed: Mar. 5, 2002

(65) Prior Publication Data

US 2003/0171813 A1 Sep. 11, 2003

(51) Int. Cl.$^7$ ................................................ A61F 2/44
(52) U.S. Cl. ................................ 623/17.11; 623/17.15; 623/17.12; 606/90; 606/99
(58) Field of Search ......................... 623/17.11, 17.12, 623/17.13, 17.14, 17.15, 17.16; 606/61, 90, 99, 86

(56) References Cited

U.S. PATENT DOCUMENTS

| | | | | |
|---|---|---|---|---|
| 5,782,832 A | * | 7/1998 | Larsen et al. | 606/61 |
| 5,951,564 A | * | 9/1999 | Schroder et al. | 606/100 |
| 6,019,793 A | * | 2/2000 | Perren et al. | 623/17.16 |
| 6,126,689 A | * | 10/2000 | Brett | 623/17.16 |
| 6,183,517 B1 | * | 2/2001 | Suddaby | 623/17.16 |
| 6,375,682 B1 | * | 4/2002 | Fleischmann et al. | 623/17.12 |
| 6,409,766 B1 | * | 6/2002 | Brett | 623/17.16 |
| 6,443,989 B1 | * | 9/2002 | Jackson | 623/17.15 |
| 6,554,864 B2 | * | 4/2003 | Ralph et al. | 623/17.11 |

* cited by examiner

Primary Examiner—Pedro Philogene
(74) Attorney, Agent, or Firm—Daniel L. Dawes; Myers Dawes Andras & Sherman LLP

(57) ABSTRACT

The spinal fusion cage of the invention comprises two opposing end plates, and three opposing collapsible legs. The two opposing end plates and three opposing collapsible legs are adapted to be configured into an expanded cage from a collapsed configuration. The expanded cage assumes a predetermined rigid shape and volume for disposition between two adjacent vertebrae. The collapsed configuration of the cage is adapted for posterior insertion into the disk space. The apparatus further comprises locking means for at least temporarily locking the legs and maintaining the cage in an expanded configuration. One of the legs is medially disposed on a first side of the cage and the other two are laterally disposed with respect to the end plates on a second side. The three legs have differing lengths so that the cage assumes a wedge-shaped envelope in the expanded configuration. The wedge-shaped envelope reestablishes a predetermined lordosis between fused vertebrae. The invention includes an inserter comprised of a tubular member and holding clamp disposed on the distal end of the tubular member. The holding clamp holds the cage in the collapsed configuration for insertion into a confined surgical theater. The cage is then reconfigured to the expanded configuration using the inserter. Further activation of the inserter causes the cage to be temporarily locked into the expanded configuration.

20 Claims, 11 Drawing Sheets

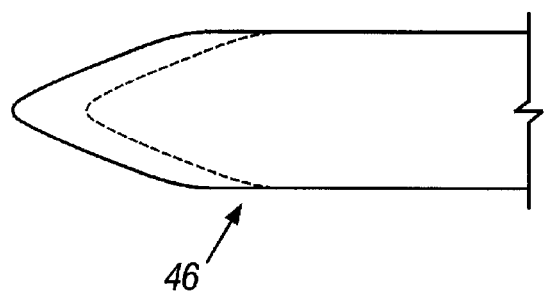
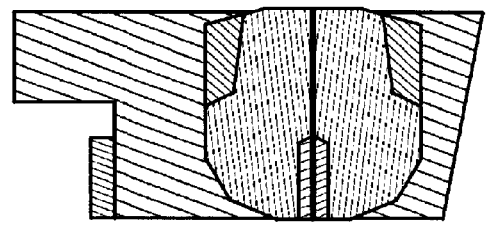
FIG. 6              FIG. 7
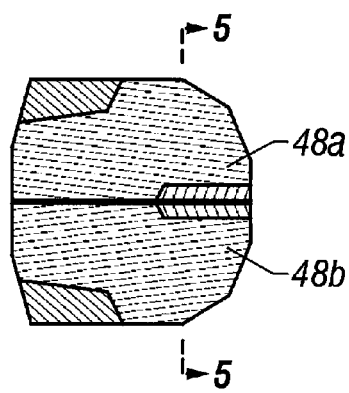
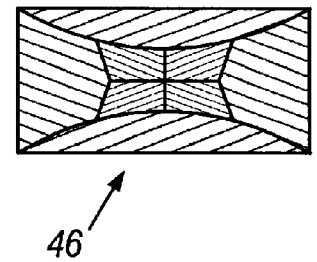
FIG. 8              FIG. 9

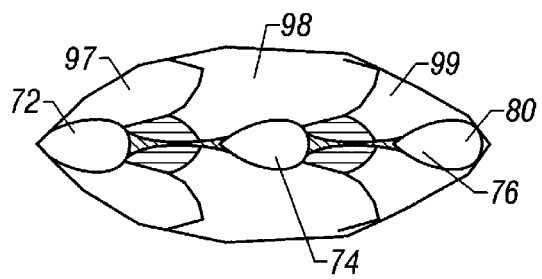
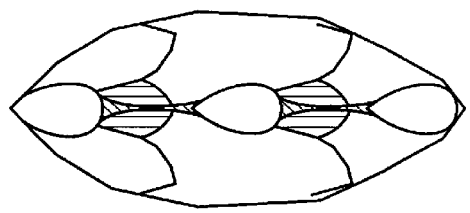
FIG. 11A  FIG. 12A
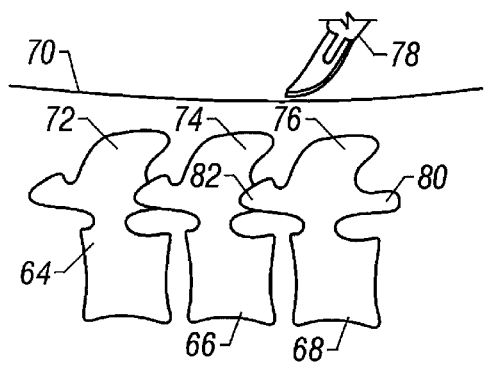
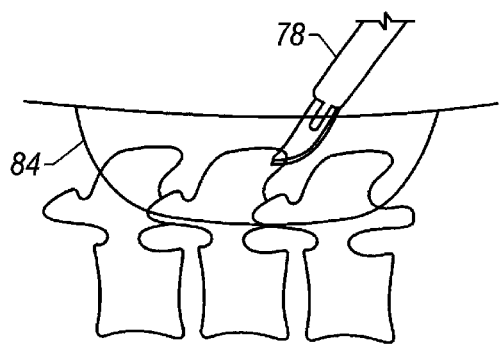
FIG. 11B  FIG. 12B
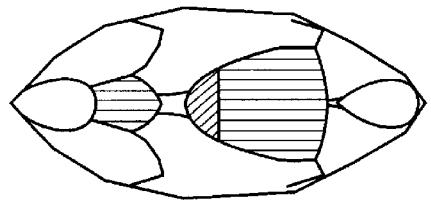
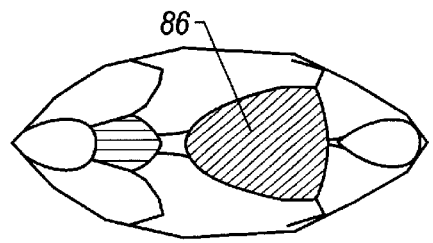
FIG. 13A  FIG. 14A
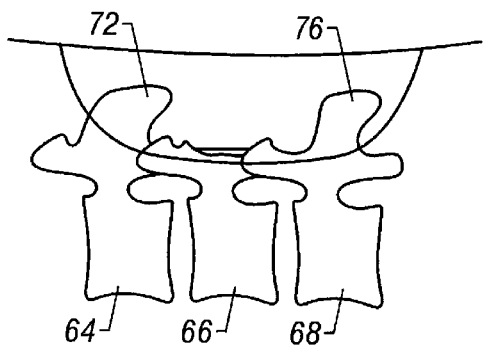
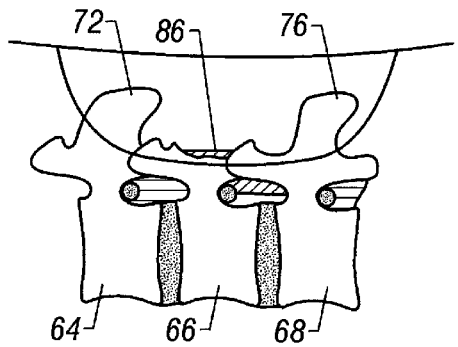
FIG. 13B  FIG. 14B

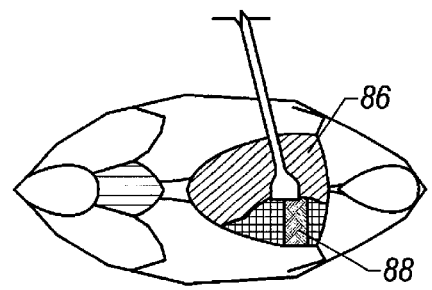
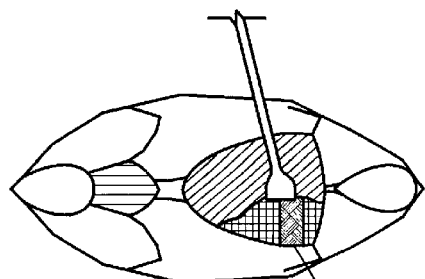
FIG. 15A  FIG. 16A
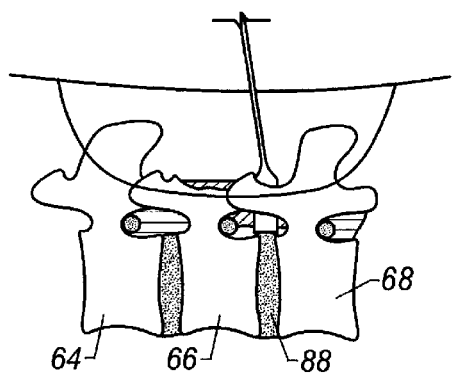
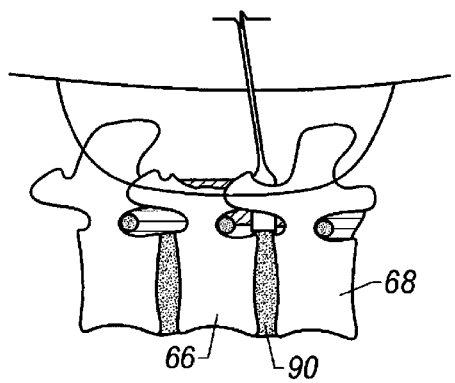
FIG. 15B  FIG. 16B
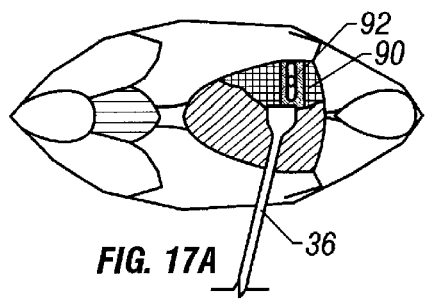
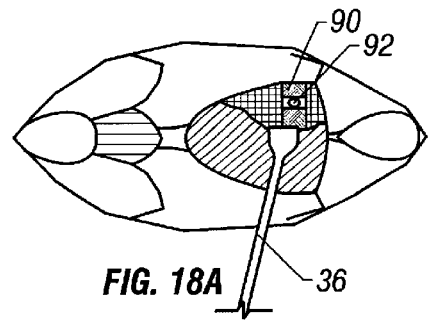
FIG. 17A  FIG. 18A
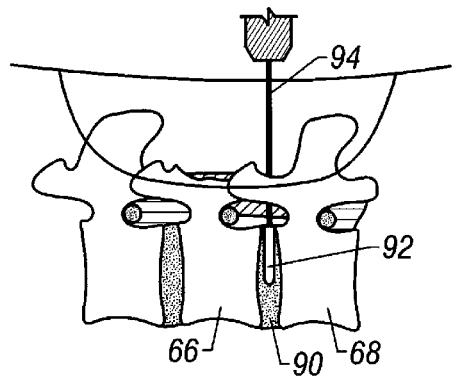
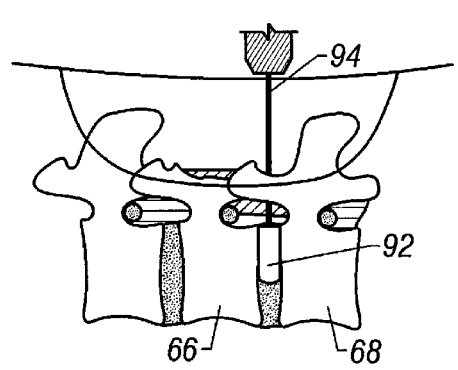
FIG. 17B  FIG. 18B

METHOD AND APPARATUS FOR PROVIDING AN EXPANDABLE SPINAL FUSION CAGE

BACKGROUND OF THE INVENTION

1. Field of the Invention

The invention relates to the field of implantable fusion cages for use in the spinal column.

2. Description of the Prior Art

Fusion cages provide a space for inserting a bone graft between adjacent portions of bone. In time, the bone and bone graft grow together through or around the fusion cage to fuse the graft and the bone solidly together. One current use of fusion cages is to treat a variety of spinal disorders, including degenerative disc diseases, Grade I or II spondylolistheses, adult coliosis and other disorders of the lumbar spine. Spinal fusion cages (included in the general term, "fusion cages") are inserted into the intervertebral disc space between two vertebrae for fusing them together. They distract (or expand) a collapsed disc space between two vertebrae to stabilize the vertebrae by preventing them from moving relative to each other.

The typical fusion cage is cylindrical, hollow, and threaded. Alternatively, some known fusion cages are unthreaded or made in tapered, elliptical, or rectangular shapes. Known fusion cages are constructed from a variety of materials including titanium alloys, porous tantalum, other metals, allograft bone, carbon fiber or ceramic material.

Fusion cages may be used to connect any adjacent portions of bone, however one primary use is in the lumbar spine. Fusion cages can also be used in the cervical or thoracic spine. Fusion cages can be inserted in the lumbar spine using an anterior, posterior, or lateral approach. Insertion is usually accomplished through a traditional open operation, but a laparoscopic or percutaneous insertion technique can also be used.

With any of the approaches, threaded fusion cages are inserted by first opening the disc space between two vertebrae of the lumbar spine using a wedge or other device on a first side of the vertebrae. Next, a tapered plug is hammered in to hold the disc space open in the case of a threaded, cylindrical cage insert. A threaded opening is then drilled and tapped on a second side opposite the first side of the vertebrae for producing the equivalent of a "split" threaded bore defined by the walls of the vertebrae above and below the bore. The threaded fusion cage is then threaded into the bore and the wedge is removed. The first side is then drilled and tapped before inserting a second threaded fusion cage. Typically, two threaded fusion cages are used at each invertebral disc level.

There are problems with all of the standard approaches. With a posterior approach, neural structures in the spinal canal and foramen need to be properly retracted before the plug is hammered or threaded into the disc space. Proper neural retraction is critical to the insertion process. If the retraction is not done properly, the procedure could cause neural injury, i.e., nerve damage and potential neurologic deficit. With either the anterior or lateral approach, blood vessels or other vital structures need to be retracted and protected to reduce or eliminate internal bleeding. Violation of the great vessels has a high mortality rate.

The general technique for inserting fusion cages is well known. Insertion techniques and additional details on the design of fusion cages is described in Internal Fixation and Fusion of the Lumbar Spine Using Threaded Interbody Cages, by Curtis A. Dickman, M. D., published in BNI Quarterly, Volume 13, No. 3, 1997, which is hereby incorporated by reference.

U.S. Pat. No. 5,782,832 to Larsen et al. (the "Larsen reference") discloses an alternate type of spinal fusion implant. FIG. 1 of the Larsen reference shows an implant apparatus with two separable support components which are adapted for adjusting sliding movement relative to each other to selectively vary the overall width of the implant to accommodate vertebral columns of various sizes or to vary the supporting capacity of the implant during healing. Each of the support components include upper and lower plate portions that are operatively connected by respective linkage mechanisms. The linkage mechanisms allow relative movement of the upper and lower plate portions between an extended position and a collapsed position. The device disclosed in the Larsen reference has several problems. One problem is that, because the width of the implant is adjusted prior to insertion, a wide insertion slot is necessary despite the reduced profile presented by the collapsed implant. Another problem is that at least part of the linkage mechanism extends beyond the upper and lower plate portions, thus requiring more invasion into the body cavity to position the implant. Yet another problem is that the linkage mechanisms must be locked into the expanded position by conventional arrangements such as locking screws.

Brett, U.S. Pat. No. 6,126,689 (2000), illustrates an expandable and collapsible fusion cage, but it design is extremely complex and therefore expensive to manufacture and prone to failure in the field. Moreover, its complex linkages require special surgical skills in its deployment. Indeed, there is no reliable deployment mechanism. The Brett design requires large hinges which make it too large and therefore unsuitable for posterior insertion.

Within the past several years there has been a dramatic resurgence of interest in interbody lumbar spinal fusions without disruption of the vertebral body endplate. Part of this renewed direction has been due to waning popularity in both anterior and posterior approach cylindrical cage fusions. Interbody fusion seems to be more reliable than the classic posterior lateral fusion for several reasons. First, the two endplates of the vertebral bodies are close together, and under compression toward each other. Second, there is a large surface area to fuse. Visualization of the nerve roots is easily done from any posterior approach.

Shortcomings have included difficulty getting lumbar Lordosis, and placing a large graft through a small hole. Trans-facet lateral fusion has recently been introduced to overcome the small hole problem. In this procedure the entire facet is removed making a much wider access to the anterior disk space. To combat the instability problems this would cause the procedure is usually done only from one side, and almost always combined with pedicle screws.

A major reason to further develop good posterior approach fusions is that it avoids the anterior surgical approach with all of its inherent risks. Indeed, it is the low but real incidence of major complications associated with the anterior surgical approach which is largely responsible for the decreasing popularity of anteriorly placed cylindrical cages.

What is needed is a simple, reliable and stable design for an insertable fusion cage and some type of inserting tool by which the implantation can be made without requiring extraordinary surgical skills which arise from the design of the fusion cage.

BRIEF SUMMARY OF THE INVENTION

The invention is an apparatus for performing spinal fusions comprising two opposing end plates; and at least two opposing collapsible legs disposed between the two opposing end plates. The two opposing end plates and at least two opposing collapsible legs are adapted to be arranged and configured into an expanded cage from a collapsed configuration. The expanded cage assumes a predetermined rigid shape and volume for disposition between two adjacent vertebrae in a disk space therebetween. The collapsed configuration of the cage is adapted to being posteriorly inserted into the disk space while preserving the facet joint. The apparatus further comprises locking means for permanently or at least temporarily locking the legs and maintaining the cage in an expanded configuration.

More particularly there are three collapsible legs in which one of the three collapsible legs is medially disposed with respect to the end plates on a first side of the cage and two of the three collapsible legs are laterally disposed with respect to the end plates on a second side of the cage. The three legs have differing lengths so that the cage assumes a wedge-shaped envelope in the expanded configuration. The wedge-shaped envelope in the expanded configuration reestablishes a predetermined lordosis between fused vertebrae, which is a normal lumbar lordosis.

In the illustrated embodiment the opposing collapsible legs are each comprised of two segments hinged together at or near one end of each segment and hinged to one of the end plates at the opposing end of each segment. The hinge coupling the two segments together at or near one end of each segment flexibly connects the two segments of each leg together. The hinge comprises a flexible strap fixed to each of the two segments and extending between the two segments. Each leg has an exterior side forming part of the exterior of the envelope of the cage and the strap fixed to each of the two segments and extending between the two segments is disposed on the two segments on the exterior side thereof so that the pivot of the corresponding collapsible leg is exterior to the envelope of the cage. As a result, the locking means comprises an over-the-center toggle for each of the at least two opposing collapsible legs. The over-the-center toggle for each of the collapsible legs comprises a resilient strap having two opposing ends. Each opposing end of the resilient strap is coupled to one of the two opposing end plates. The strap is coupled to a corresponding collapsible leg so that when the cage is in the expanded configuration, the resilient strap applies a compressive force to the corresponding collapsible leg to maintain the corresponding collapsible leg in a locked configuration. The collapsible legs are each comprised of two segments hinged together at or near one end of each segment and hinged to one of the end plates at the opposing end of each segment and wherein each leg has an exterior side forming part of an exterior of an envelope of the cage and wherein the resilient strap is disposed on the two segments on the exterior side thereof. The two segments comprising a collapsible leg is coupled to the end plates by an open hinge.

The invention further comprises an inserter comprised of a tubular member having a distal end and holding clamp disposed on the distal end of the tubular member. The holding clamp is adapted to hold the cage in the collapsed configuration for insertion into a confined surgical theater of operation. Then on selective activation by the tubular member the cage is configured from the collapsed configuration to the expanded configuration. The activation of the tubular member the cage is permanently or at least temporarily locked into the expanded configuration. The inserter comprises a grip, and actuation or movement of the grip by a first amount configures the cage in the expanded configuration. Actuation or movement of the tubular member by a second successive amount locks the cage in the expanded configuration.

The tubular member comprises a hollow tubular housing and a telescopic rod disposed in the hollow tubular housing. The holding clamp is resiliently coupled to the tubular housing. The telescopic rod engages the holding clamp to manipulate the holding clamp to configure the cage from the collapsed configuration to the expanded configuration when the telescopic rod engages the holding clamp. The telescopic rod selectively engages the collapsible legs to configure the legs into a self-locked configuration.

The invention also comprises a method of using the cage and inserter described above to perform posterior spinal fusions.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

FIG. 6 is top plan view of the distal end of the telescopic rod in the inserter shown in FIG. 5.

FIG. 7 is a bottom plan view of one of the two jaws of the holding clamp as seen through lines 7—7 of FIG. 5.

FIG. 8 is a transverse end view of the two jaws of the holding clamp as seen through lines 8—8 of FIG. 5.

FIG. 9 is an end plan view of the end of the telescopic rod in the inserter as seen through lines 9—9 of FIG. 5.

FIG. 11a is a plan posterior view or top view, looking down on the back of the patient, of the surgical theater of operation and FIG. 11b is the corresponding simplified side plan view of the underlying tissues in the surgical theater of operation prior to any operative step.

FIG. 12a is a plan posterior view of the surgical theater of operation and FIG. 12b is the corresponding simplified side plan view of the underlying tissues in the surgical theater of operation after the first operative step of approach or incision.

FIG. 13a is a plan posterior view of the surgical theater of operation and FIG. 13b is the corresponding simplified side plan view of the underlying tissues in the surgical theater of operation after laminectomy.

FIG. 14a is a plan posterior view of the surgical theater of operation and FIG. 14b is the corresponding simplified side plan view of the underlying tissues in the surgical theater of operation after the ligamentum flavum has been removed.

FIG. 15a is a plan posterior view of the surgical theater of operation and FIG. 15b is the corresponding simplified side plan view of the underlying tissues in the surgical theater of operation after the dura and nerve root has been retracted.

FIG. 16a is a plan posterior view of the surgical theater of operation and FIG. 16b is the corresponding simplified side plan view of the underlying tissues in the surgical theater of operation after the disk has been removed.

FIG. 17a is a plan posterior view of the surgical theater of operation and FIG. 17b is the corresponding simplified side plan view of the underlying tissues in the surgical theater of operation after the spacer has been inserted.

FIG. 18a is a plan posterior view of the surgical theater of operation and FIG. 18b is the corresponding simplified side plan view of the underlying tissues in the surgical theater of operation after the spacer has been rotated to distract the disk space.

Figure 1:
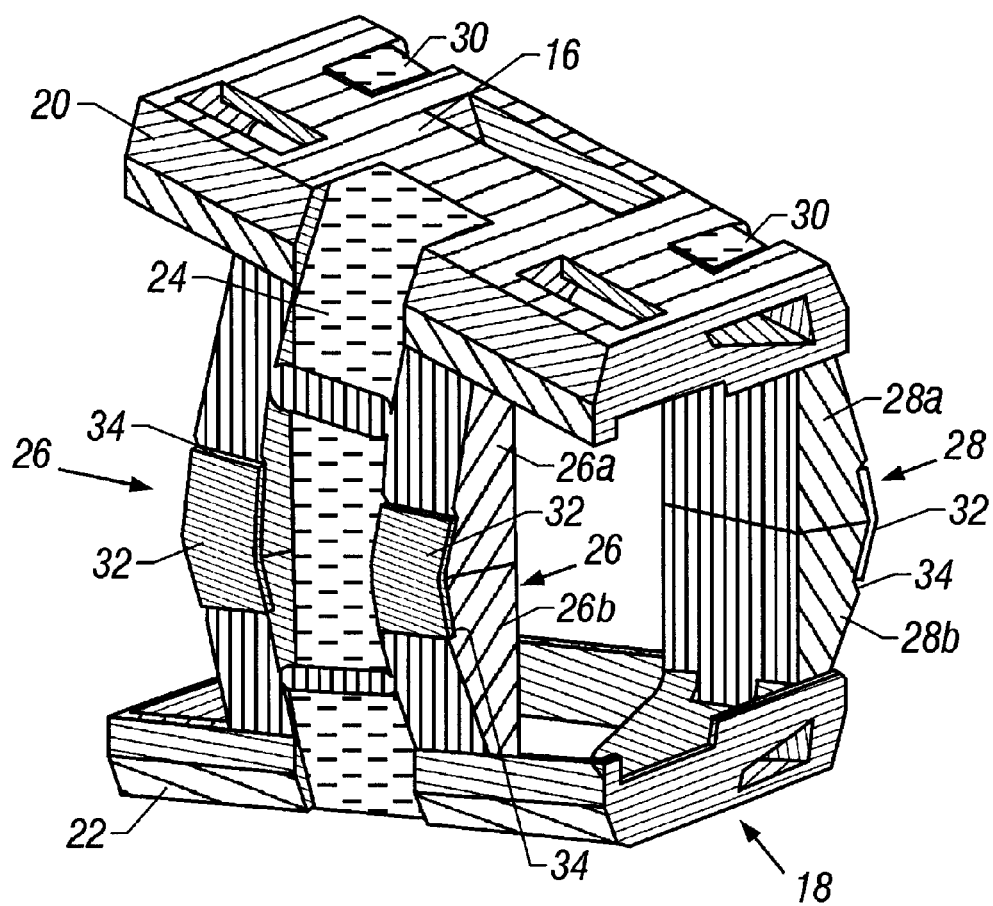
FIG. 1 is a perspective view of the fusion cage of the invention shown in the expanded configuration.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

The spinal fusion cage of the invention comprises two opposing end plates, and three opposing collapsible legs. The two opposing end plates and three opposing collapsible legs are adapted to be configured into an expanded cage from a collapsed configuration. The expanded cage assumes a predetermined rigid shape and volume for disposition between two adjacent vertebrae. The collapsed configuration of the cage is adapted for posterior insertion into the disk space. The apparatus further comprises locking means for permanently or at least temporarily locking the legs and maintaining the cage in an expanded configuration. One of the legs is medially disposed on a first side of the cage and the other two are laterally disposed with respect to the end plates on a second side. The three legs have differing lengths so that the cage assumes a wedge-shaped envelope in the expanded configuration. The wedge-shaped envelope reestablishes a predetermined lordosis between fused vertebrae. The invention includes an inserter comprised of a tubular member and holding clamp disposed on the distal end of the tubular member. The holding clamp holds the cage in the collapsed configuration for insertion into a confined surgical theater. The cage is then reconfigured to the expanded configuration using the inserter. Further activation of the inserter causes the cage to be temporarily locked into the expanded configuration. Collapse and removal of the device, should that become necessary, is accomplished by squeezing the medial and lateral legs together using a standard surgical clamp.

Characteristics of the Expandable Lumbar Cage

Before describing the illustrated embodiment in detail and its method of deployment, first consider some general features, which characterize cage 10 of the invention. The device or expandable cage 10 of the illustrated embodiment easily fits into the disk space with minimal resection of the facet joints. About 10 mm in width is the maximum that will normally readily fit. The expandable cage 10 fits between the end plates of the vertebral bodies into the disk space. In this dimension 6 mm will go in comfortably in even difficult cases. The depth is about 25 mm (1 inch). This has been shown with many allografts to be a good universal length.

Once inserted into the disk space cage 10 should expand in height enough to distract the ligaments, open the neuroforimen, and stabilize the spine. Typically 10–14 mm is needed. The proposed device's expansion limit in the illustrated embodiment is 18 mm.

Once inserted cage 10 is expanded as described below into a wedged shape to reestablish normal lumbar lordosis. This is performed by expanding the deep end 12 of cage 10 more than the near end 14 as best shown in FIG. 10b. Once expanded the top surface 16 of cage 10 is inclined about 11° with respect to the bottom surface 18 to make a wedge shape. The larger end 12 goes toward the front of the disk space (from posterior, the wide or larger end 12 goes in deep).

Currently posterior lumbar interbody fusions (PLIFs) get around the natural disk space wedging by cutting a groove through the posterior vertebral bodies and end plates to create a rectangular groove for rectangular device or bone graft insertion, or by placing more graft or a vertical cage in the front of the disk space, or by cutting the graft into a wedge and then rotating into place once in the disk space. All of these methods, almost by necessity, must sacrifice the facet joint in order to get their large device into the disk space, cannot be rigid, or remove large portions of the weight bearing endplate.

Cage 10 of the invention once deployed must resist compression, rotation, as well as side to side and end to end rocking. It also includes a provision for removal as described below. Once deployed cage 10 is wide open thereby allowing large amounts of space for packing bone graft materials. Cage 10 is easy to manufacture, and to deploy reliably and consistently.

Structure of the Expandable Cage

In the illustrated embodiment cage 10 is a small (10 mm×6 mm×25 mm), expandable device suitable for inserting into the disk space from the spinal canal posteriorly. Cage 10 once expanded is open in the center, allowing ample space for placement of bone graft. Cage 10 may be made of several materials, however, titanium is preferred for strength, bone in-growth, modulus of elasticity, and MRI/X-ray/CT compatibility post-operatively.

Once deployed cage 10 expands to a maximum 18 mm in height (exact height must be selected before insertion as discussed below), and recreates about 11° of lumbar lordosis. Cage 10 is highly stable to all likely forces to which it will be subjected once it is deployed.

Cage 10 is comprised of two a top and a bottom exterior surface 16 and 18 respectively as shown in FIG. 1 defined by two end plates 20 and 22. The top and bottom plates 20 and 22 are mirror images of each other. Each one is milled or formed as a solid piece. End plates 20 and 22 are spaced apart by two narrow, medial hinged legs 28, only one of which is visible in FIG. 1, one wide, lateral hinged leg 26, and three flexible metal straps 24 and 30, which connect the top plate 20 to bottom plate 22 by passing through the hinged legs 26 and 28, one strap 24 through the center of leg 26 and one strap 30 through the center of each of the two legs 28.

Each of the legs 26 and 28 are composed of a segment 26a or 28a and its mirror image 26b and 28b in the case of legs 26 and 28 respectively, which segments joined at their adjacent ends by flexible adhesive or as shown in FIG. 1 by a strap hinge 32 of material the same or similar to that used for straps 24 and 30. A channel or indentation 34 is defined in segments 26a, 26b, 28a, 28b to provide for a space for strap hinge 32 so that it forms part of a flush exterior surface for each leg 26 and 28. The strap placement also helps pull the legs into position during deployment, and lock them open after deployment. The strap also pushes leg 28 into its articulation with top end plate 20 or bottom end plate 22. The straps 24, 30 and 32 are flexible, thin metal strips and have a small degree of elasticity e.g. about 5% stretch from resting length.

The Expansion Process

An insertion device or inserter, generally denoted by reference numeral 36, and best shown and described below in connection with FIGS. 5–10 orients cage 10 to the endplates of the vertebrae and establishes the depth of insertion. Once inserted and held in the desired location, the surgeon squeezes a handle which opens cage 10 and then locks legs 26 and 30 into place. Should removal be necessary, the device is easily unlocked for removal.

Figure 2:
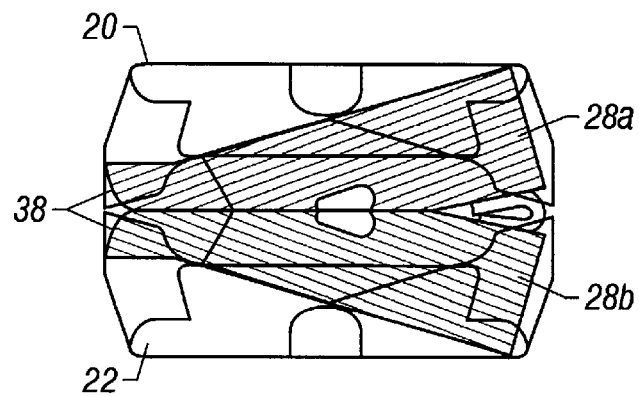
FIG. 2 is an end plan elevational view of the cage of FIG. 1 in the collapsed configuration showing one collapsed leg.
Figure 10:
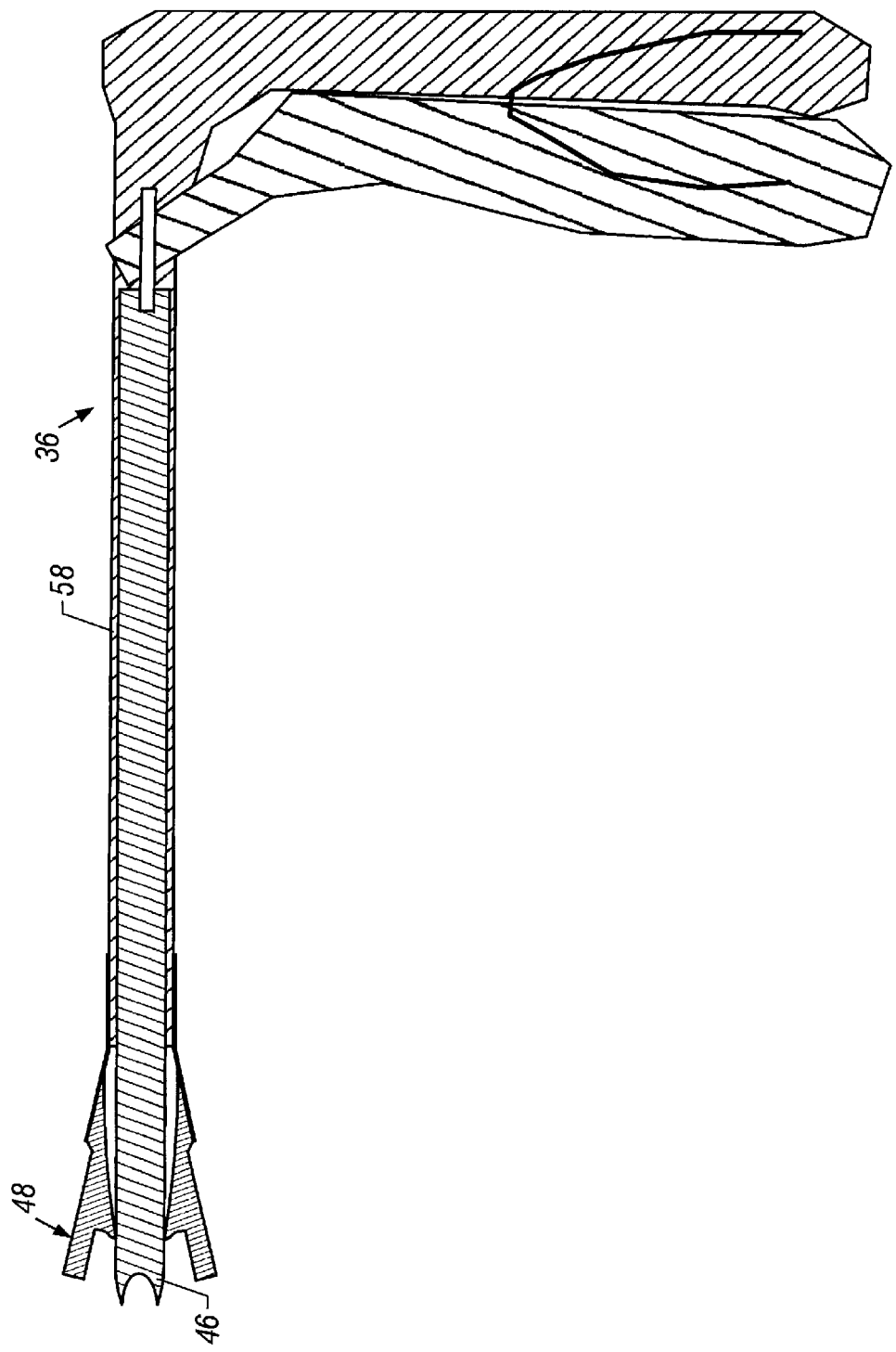
FIG. 10 is a side cross-sectional view of the inserter of the invention used to insert the cage of FIG. 1 between vertebrae shown in the fully extended configuration.

Consider now in more detail the expansion of cage 10. Legs 26 and 28 are folded inside or between the top and bottom plates 20 and 22 as shown in the end view of FIG. 2, wherein one leg 28 is depicted, when cage 10 is in its collapsed configuration. Straps 24 and 30 run through legs 26 and 28 respectively. The top and bottom plates 20 and 22 are sealed together with a very light adhesive (not shown) to prevent premature deployment. The insertion device 36 pushes the top and bottom plates 20 and 22 apart as shown in FIG. 10 toward the vertebral body endplates breaking the adhesive. The two segments 26a, 26b of leg 26 and the two segments 28a and 28b of legs 28 are hinged in their middle by straps 34.

Figure 3:
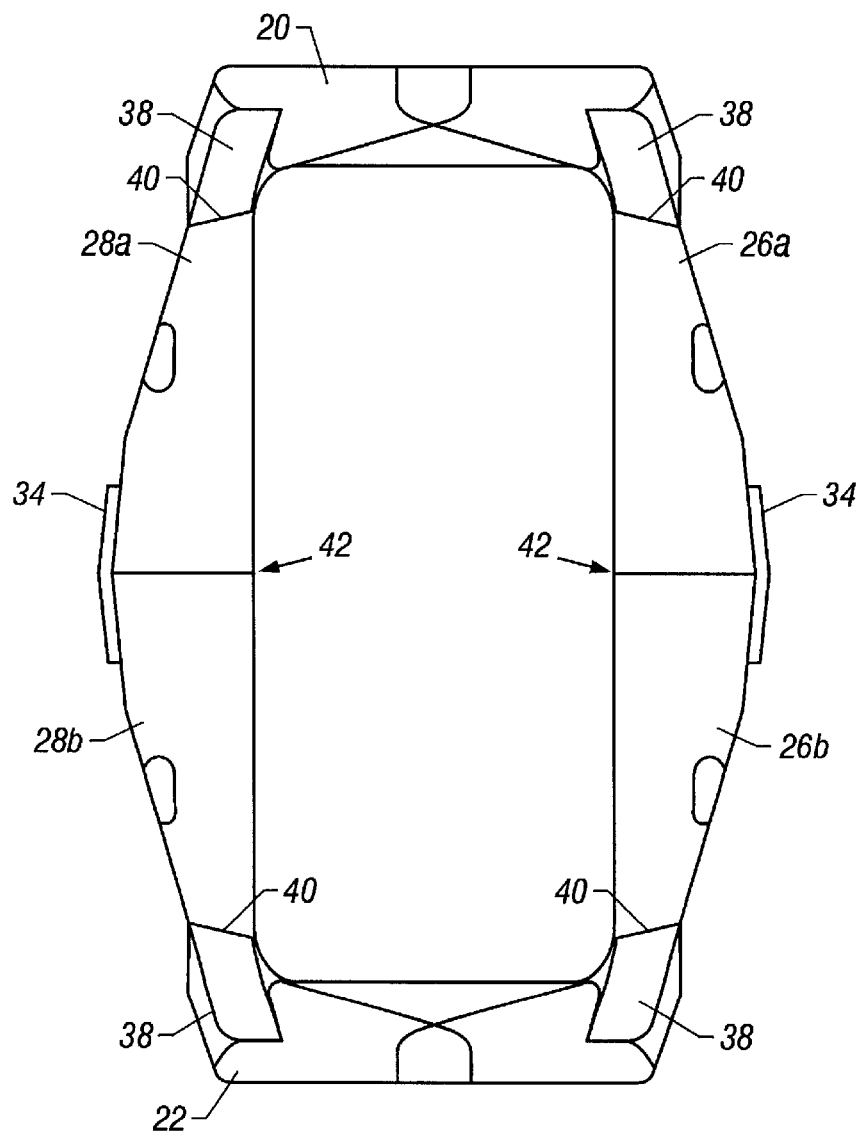
FIG. 3 is an end plan elevational view of the cage of FIG. 1 in the expanded configuration showing two locked legs.
Figure 4E:
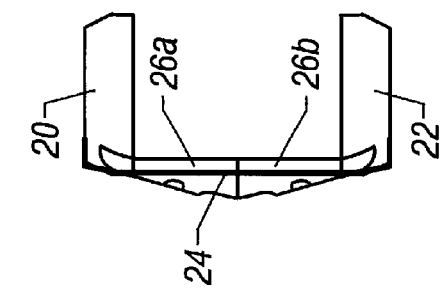
FIGS. 4a–4e is a series of simplified ends view of the end plates and one collapsible leg with its resilient strap illustrating the sequence of steps from the collapsed configuration to the expanded configuration and vice versa.
Figure 4D:
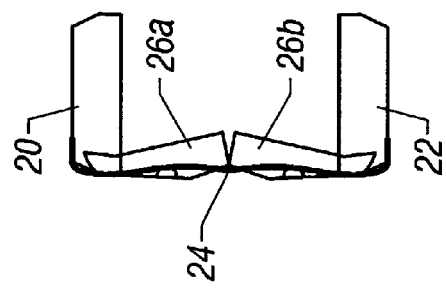
Figure 4C:
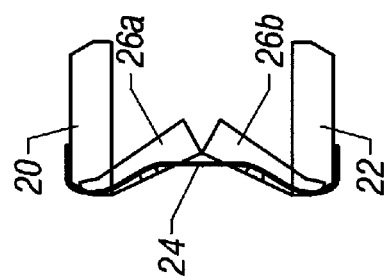
Figure 4B:
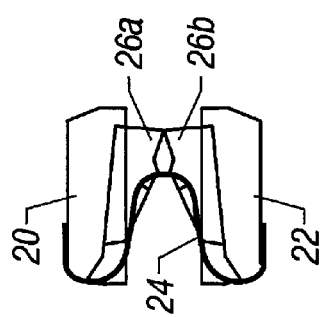
Figure 4A:
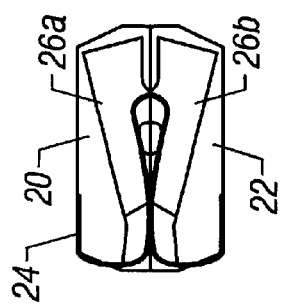

As the top and bottom plates 20 and 22 separate to assume the position shown in the end view of FIG. 3, the legs 26 and 28 are forced open or outward from the interior of cage 10 in a toggling action by the stretching and tightening of straps 24 and 30 between the top and bottom endplates 20 and 22. Inserter 36 does the final locking maneuver as discussed below. FIGS. 4a–4e graphically represent the process of expanding cage 10 and show the motion of only a single leg 26 relative to plates 20 and 22 for simplicity. FIG. 4a is the completely collapsed configuration of FIG. 2. FIG. 4e is the completely expanded configuration of FIG. 3. FIGS. 4b–4d represent configurations of cage 10 as it is being expanded between the completely collapsed configuration of FIG. 2 and the completely expanded configuration of FIG. 3. Strap 24 threaded through leg 26 between plates 20 and 22 is shown in dark line for emphasis. In FIG. 4b plates 20 and 22 are just beginning to be separated by inserter 36 (not shown) and leg segments 26a and 26b are being pulled down from plate 20 and up from plate 22 by the straightening of strap 24. In FIG. 4c as strap 24 continues to be straightened as inserter 36 continues to separate plates 20 and 22, segments 26a and 26b are pulled outward from the center of cage 10 and ends 38 are moved to place shoulders 40 into contact with opposing surfaces on plates 20 and 22. In FIG. 4d strap 24 has been stretched to its extent to which it will be stretched during the expansion or opening phase of cage 10 as graphically shown in the distance of separation of plates 20 and 22 in FIG. 4d. At this point in time the exterior corners of the center edges 42 of segments 26a and 26b are in contact with each other and the opposing shoulders 40 of ends 38 of segments 26a and 26b are in contact with the adjacent surfaces of plates 20 and 22. As will be discussed in greater detail in connection with FIG. 10 the disposition of a locking rod 44 in inserter 36 into the interior of cage 10 forces segments 26a and 26b further outboard and the relaxation of the separation of plates 20 and 22 allows center 42 of segments 26a and 26b to flushly contact each other and snap into place in a toggling action to result in the configuration of FIG. 4e. This allows strap 24 is contract to a degree and the center of rotation of segments 26a and 26b to move outboard from strap 24. The continued tension of strap 24 thus tends to maintain segments 26a and 26b in a locked flush juxtaposition with each other as shown in FIG. 4e. Using a surgical clamp to squeeze the legs medially inwards allows for the expansion of plates 20 and 22 and the inward rotation of segments 26a and 26b into the interior of cage 10 to reverse the motions serially depicted in FIGS. 4a–4e. The same sequence of motions of course occur in a similar manner with leg segments 28a and 28b.

The tautness of straps 24 and 30 also pushes the top and bottom ends 38 of legs 26 and 28 into the top and bottom plates 20 and 22. The top and bottom ends 38 of legs 26 and 28 use an open hinge for several reasons. First, these are very small structures. Placing a metal pin through them to make a standard hinge would take up far too much space, and weaken the structure. Second, the open hinge allows a more compact collapsed profile for cage 10. The open hinge allows for three-point fixation which greatly stabilizes and strengthens legs 26 and 28 once they are locked into place. Should removal be necessary, legs 26 and 28 of cage 10 are easily unlocked for removal.

The primary weight bearing surface is through the "shoulders" 40 of legs 26 and 28. The central portion 42 of legs 26 and 28 pushes toward the center or interior of cage 10, while the weight on cage 10 from the vertebrae, and the elasticity of straps 24 and 30 pull top and bottom plates 20 and 22 toward each other and tends to push legs 26 and 28 out or away from the center or interior of cage 10. Legs 26 and 28 are pushed out because the strap hinge 34 connecting the two halves 26a and 26b of leg 26 and the two halves 28a and 28b of leg 28 are outside of the center of rotation and the center of gravity of leg 26 and 28. Thus straps 24 and 30 rest in tension and weight bearing legs 26 and 28 oppose the tension, making cage 10 a very stable structure. As stated, the primary weight-bearing goes through both shoulders 40 of each leg 26 and 28.

The Inserter

One element in making cage 10 practical is having a reliable, simple method to open cage 10 and lock legs 26 and 28 open as described in connection with FIGS. 4a–4e once cage 10 is in place. Inserter performs 36 both functions of opening and locking legs 26 and 28 with a single motion. Inserter 36 is strong enough to at least partially distract the disk space, compact enough so it will fit into a hole no larger than what is needed for cage 10 itself, and reliable enough so that once deployed, there must be certainty that legs 26 and 28 are locked open.

As shown in FIGS. 5–10 inserter 36 works by pushing a wedge-shaped distal end 46 first into a clamp 48 holding cage 10, which starts the deployment. Then wedge-shaped distal end 46 of rod 44 continues into the interior of cage 10 between legs 26 and 28 of cage 10 forcing them outwardly to the side, and firmly locking them into place. To remove cage 10 a clamp (not shown) is placed over legs 26 and 28 to squeeze them together, which unlocks cage 10.

Figure 5:
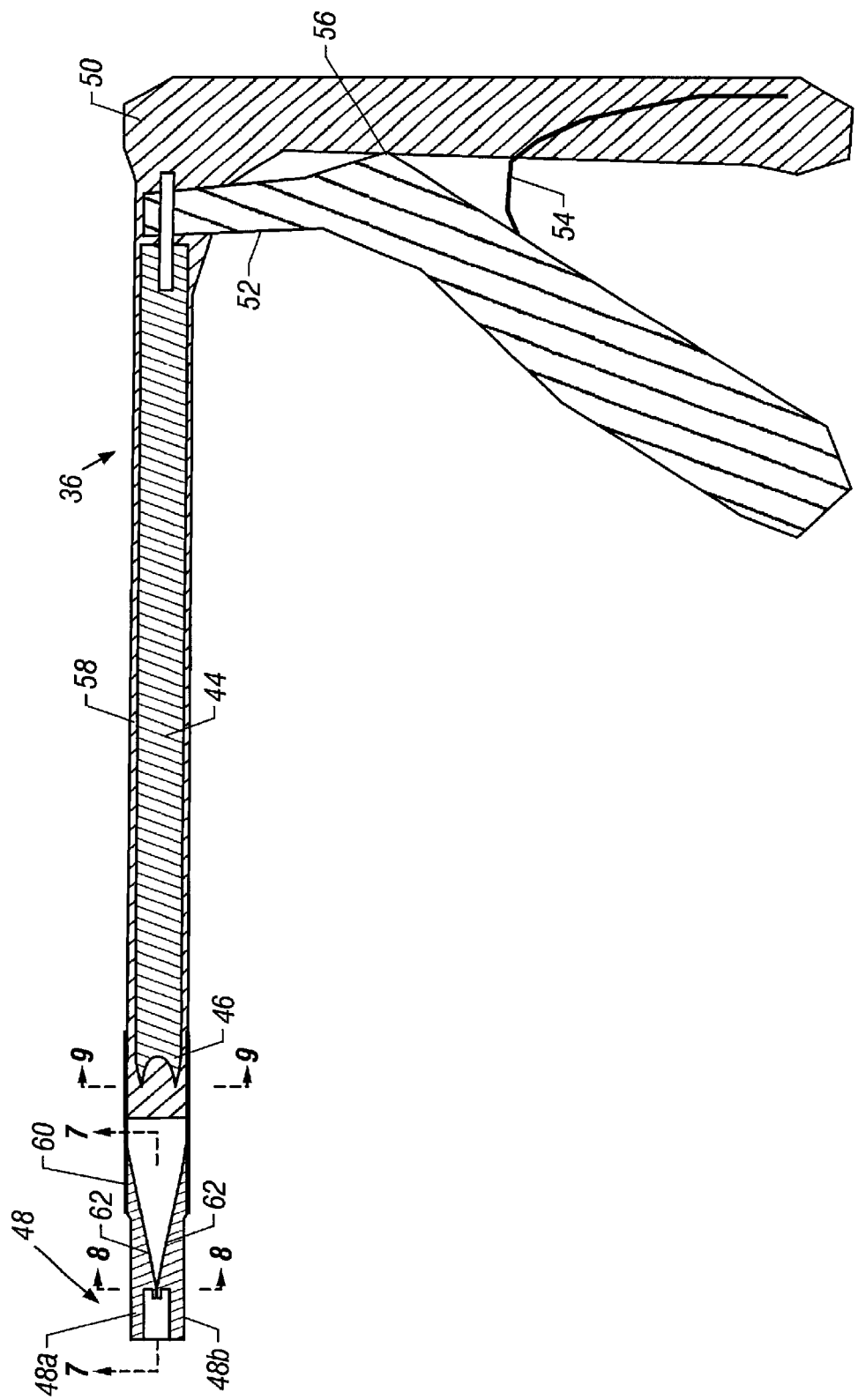
FIG. 5 is a side cross-sectional view of the inserter of the invention used to insert the cage of FIG. 1 between vertebrae shown in the fully retracted configuration.

More particularly, FIG. 5 is a side cross-sectional view of inserter 36 which takes the form of a stationary pistol grip 50 with a posterior squeeze lever 52 rotatably connected to grip 50 and resiliently biased by spring 54 to the open position. Squeezing lever 52 against grip 50 against spring 54 rotates lever 52 about pivot point 56 to push rod 44 telescopically forward within tube 58. The distal end 46 of rod 44 is wedge shaped in both its lateral and vertical aspects as shown in FIG. 9. In other words, the wedge is formed both as a function of the distance from a longitudinal axis of symmetry, denoted as the z axis, in both the orthogonal x and y axis directions as one moves toward the distal tip 46 of rod 44. In the illustrated embodiment the slope of the wedge in one of the x and y axis directions is steeper than in the other, although the invention contemplates both equal and unequal wedge shapes. Rod 44 is oriented by virtue of the orientation of grip 50 so that the amount of separation of plates 20 and 22 are determined by the degree of the wedge in one direction brought to bear against the interior surfaces of plates 20 and 22, while the amount of separation of legs 26 and 28 are determined by the degree of the wedge in the orthogonal direction brought to bear against the interior surfaces of legs 26 and 28.

Cage 10 (not shown in FIGS. 5 and 10) is held by clamp 48, which is attached to tube 58 by means of an elastomeric sleeve 60, which telescopically overlaps and is fixed to the distal end of tube 58 and the proximal end of clamp 48. Clamp 48 is comprised of a two piece set of jaws 48a and 48b. Jaws 48a and 48b are shown in longitudinal cross section in FIG. 5 as would be seen through section 5—5 of FIG. 8 as comprising the distal end of inserter 36. An interior plan view as seen through lines 7—7 of FIG. 5 of one of the jaws 48a is depicted in FIG. 7. A transverse cross-sectional view of the two opposing jaws 48a and 48b as taken through section lines 8—8 of FIG. 5 is shown in FIG. 8. Jaws 48a–48d may have complexly curved shape to match or key into conforming surfaces of cage 10 as desired. The salient feature of jaws 48a and 48b is that as distal end 46 of wedge-shaped rod 44 is pushed forward, the wedge surfaces contact inner surfaces 62 of jaws 48a and 48b to splay jaws 48a and 48b outwardly from the longitudinal axis of cage 10 and aligned tube 58 so that plates 20 and 22 are separated and ultimately assume the configuration of FIG. 4d. Plates 20 and 22 assume the configuration of FIG. 4d by virtue of the opening of jaws 48a and 48b due to their spreading caused by the wedge in the plane of FIG. 5 on distal end 46 of rod 44. When as shown in FIG. 10 rod 44 is further extended beyond jaws 48a and 48b, jaws 48a and 48b do not spread further because they are in contact with the uniform cross section of rod 44. However, the wedge shape of distal end 46 of rod 44 as it extends in the orthogonal direction out of the plane of FIG. 5 then comes into contact with center 42 of legs 26 and 28, which are pushed outwardly in preparation to lock as shown in FIG. 4e. The withdrawal of rod 44 back into tube 58 allows strap 24 to relax, plates 20 and 22 to move toward each other as jaws 48a and 48b close, and to lock leg segments 26a, 26b and 28a, 28b into place as shown in FIG. 4e.

End to end stability has not been a problem with most grafts. Rolling or side to side stability is present because of the cantilevered hinges or ends 38 which cannot rotate once cage 10 is deployed. Half of the hinges or ends 38 are always resisting any side-to-side moment.

Because cage 10 is essentially open, there is ample space for bone grafting. What this allows is stable interbody fusion in the spine from the back, while preserving the facet joints. In applications where cage 10 is exceptionally stable, then it is possible to use cage 10 for stand alone fusions, obviating the need for pedicle screws.

The Use of the Cage in Lumbar Fusions

Cage 10 and inserter 36 and their operation now having been described in detail, consider how they are used in an actual posterior interbody lumbar fusion. FIGS. 11a and 11b a simplified diagrams showing vertebrae 64, 66, and 68 below posterior skin surface 70 with spinous processes 72, 74, and 76 and lamina 97, 98, 99 respectively. Each vertebra 64, 66, and 68 has a spinous process 80 and a superior articular process 82 shown in FIG. 11b for vertebra 68. The surgical approach is made as shown in FIGS. 12a and 12b where scalpel 78 is used to cut to a line 82 to the depth of the processes of vertebrae 64, 66, and 68. A laminectomy is then performed as shown at FIGS. 13a and 13b where the spinous process 74 and lamina 98 of vertebra 66 are removed to provide access to at least one side of vertebra 66. The spinal dura is, however, still encased by substantial overlying soft tissue structures. The ligamentum flavum 86 is removed as shown in FIGS. 14a and 14b. In FIGS. 15a and 15b the dura and nerve root is retracted to the side to expose the disk 88 between vertebrae 66 and 68. The disk 88, which is diseased, or separates vertebrae 66 and 68 which must be fused, is surgically removed in FIGS. 16a and 16b to leave the disk space 90 open between vertebrae 66 and 68.

Figure 19A:
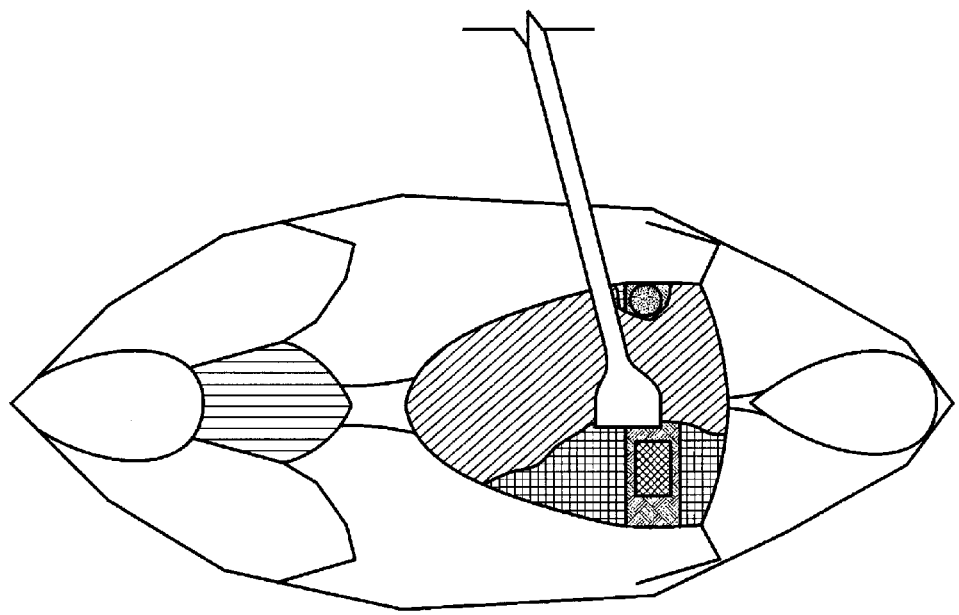
FIG. 19a is a plan posterior view of the surgical theater of operation and FIG. 19b is the corresponding simplified side plan view of the underlying tissues in the surgical theater of operation after the cage of the invention has been inserted into the disk space.
Figure 19B:
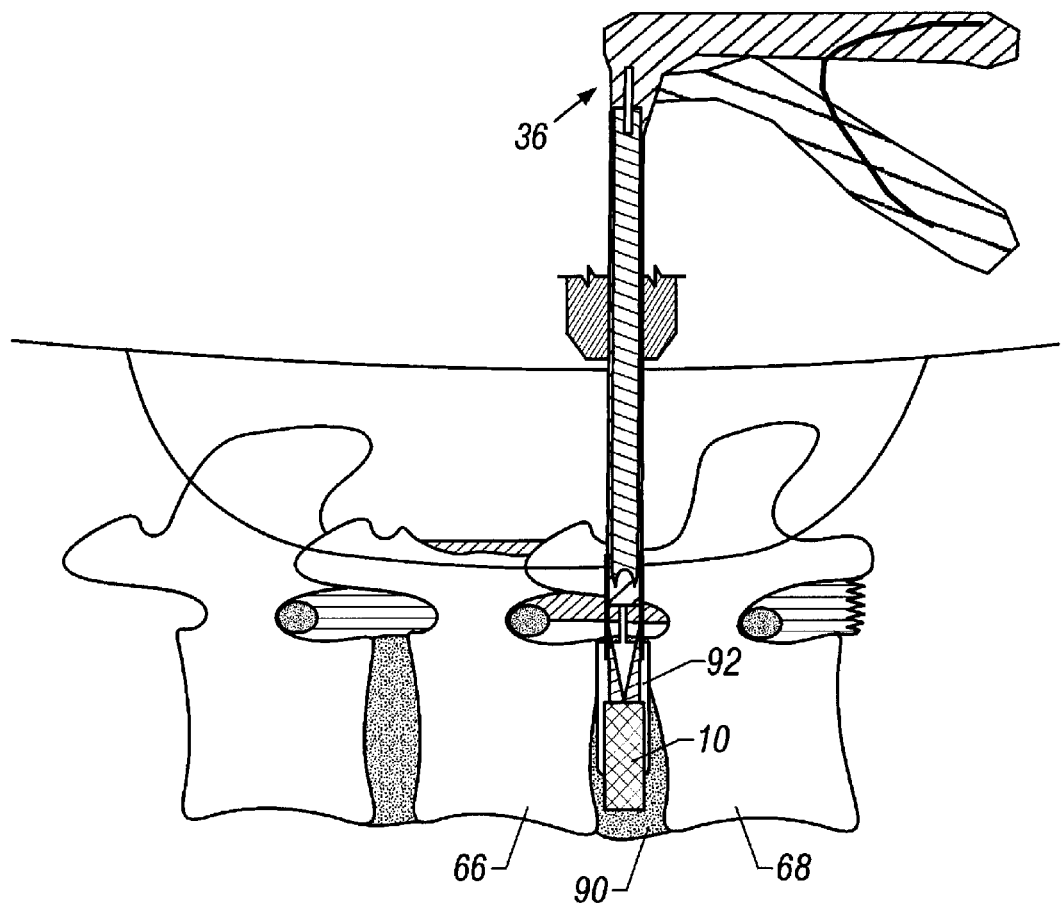
Figure 20A:
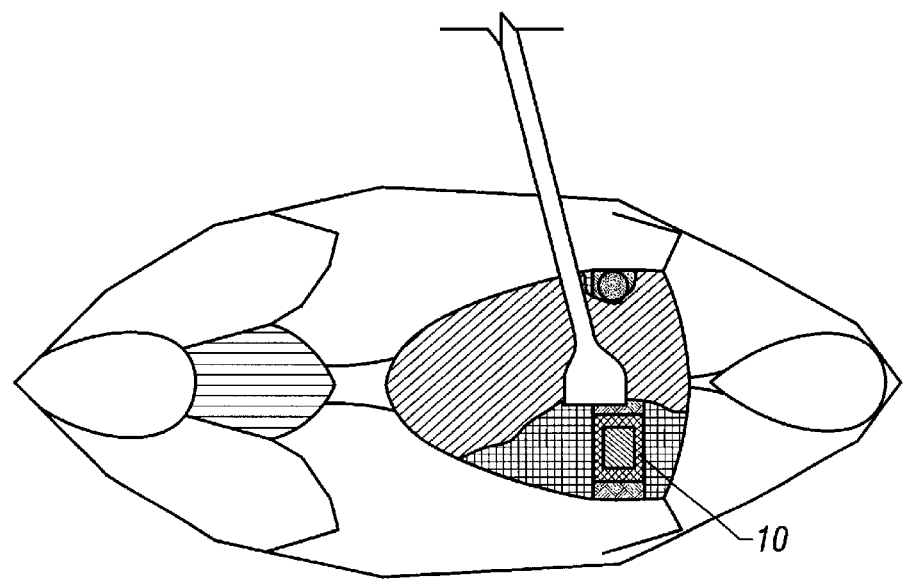
FIG. 20a is a plan posterior view of the surgical theater of operation and FIG. 20b is the corresponding simplified side plan view of the underlying tissues in the surgical theater of operation after the cage of the invention has been expanded in the disk space.
Figure 20B:
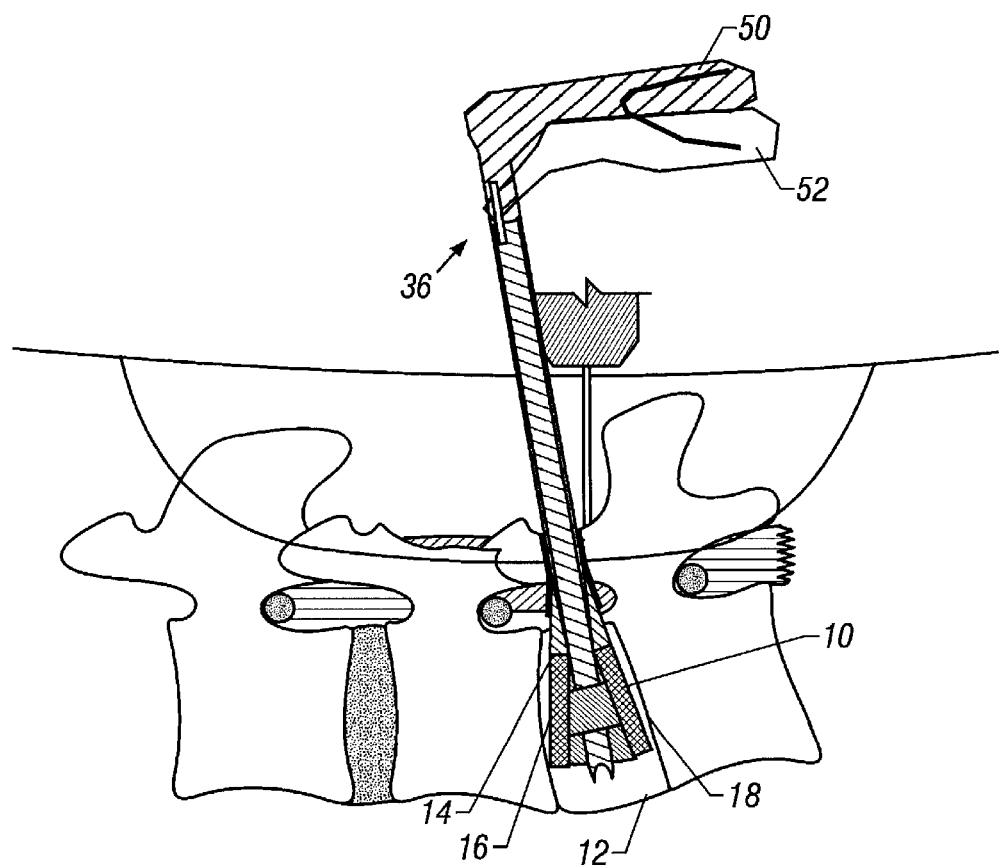
Figure 21A:
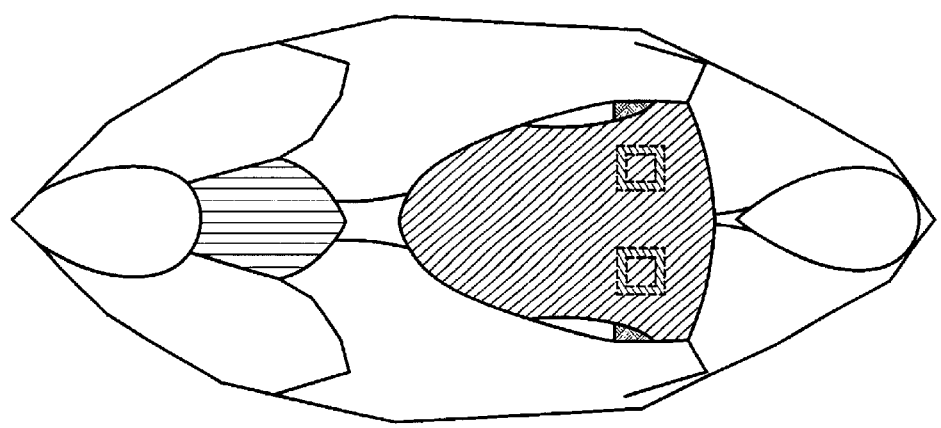
FIG. 21a is a plan posterior view of the surgical theater of operation and FIG. 21b is the corresponding simplified side plan view of the underlying tissues in the surgical theater of operation after the inserter and spacer has been removed and after the cage of the invention has been implanted on each side of the disk space.
Figure 21B:
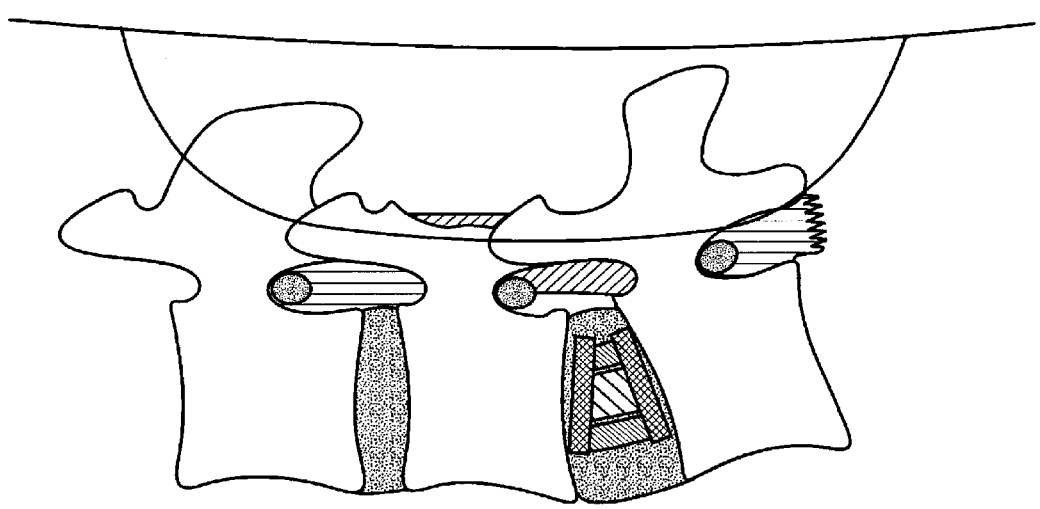

In FIGS. 17a and 17b a flattened spacer 92 affixed to the end of rod 94 is disposed into disk space 90 with its smallest or flattest dimension parallel to end plates of vertebrae 66 and 68. Spacer 92 is then rotated 90° by rotating rod 94 to orient the largest dimension of spacer 92 between vertebrae 66 and 68 so that vertebrae 66 and 68 are spaced apart from each other by a predetermined distance which is slightly greater than the thickness of cage 10 as shown in FIGS. 18a and 18b. Inserter 36 is then used to place cage 10 to the side of spacer 92 in disk space 90 as shown in FIGS. 19a and 19b. Cage 10 is oriented between vertebrae 66 and 68 so that end plates 20 and 22 are position adjacent to the end plates of vertebrae 66 and 68. Lever 52 is activated as described above in connection with FIG. 5 and cage 10 is expanded as described in connection with FIGS. 4a–4e. As can be readily seen in Fib. 20b the design of legs 26 and 28 and jaws 48a and 48b of inserter 36 expand and lock the configuration of cage 10 to assume a predetermined wedge shape to reestablish normal lumbar lordosis, which is otherwise lost, resulting in flat back syndrome. Spacer 92 and inserter 36 are then removed leaving expanded cage 10 implanted between vertebrae 66 and 68.

The same procedure is performed on the opposing side of the endplates of vertebrae 66 and 68 to dispose a pair of cages 10 in a balanced manner on each side of the spinal cord and to provide stable support. Bone graft material and/or other medicaments are then disposed in disk space 90 and into the interior of cages 10 to complete the lumbar fusion in a conventional manner.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, although the resilient, flexible straps 24, 30, 34 of cage 10 have been described as being comprised of metal, preferably titanium, it is also within the scope of the invention to use other resilient and flexible materials including elastomeric polymers. Cage 10 has been shown with a particular detailed surface structure to conform to jaws 48a and 48b of inserter 36, but it is again to be understood that the detailed structure of cage 10 can be altered in many different ways according to design options, while still falling within the teachings of the invention.

For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

I claim:

1. An apparatus for spinal fusions comprising:

two opposing end plates; and at least two opposing collapsible legs disposed between the two opposing end plates, the two opposing end plates and at least two opposing collapsible legs adapted to be arranged and configured into an expanded cage from a collapsed configuration in which the expanded cage assumes a predetermined rigid shape and volume for disposition between two adjacent vertebrae in a disk space therebetween, and in which collapsed configuration the cage is adapted to being posteriorly inserted into the disk space, wherein the at least two opposing collapsible legs are each comprised of two segments hinged together at or near one end of each segment and hinged to one of the end plates at the opposing end of each segment, wherein the hinge coupling the two segments together at or near one end of each segment flexibly connect the two segments of each leg together, wherein the hinge coupling the two segments together at or near one end of each segment flexibly connect the two segments of each leg together.

2. The apparatus of claim 1 wherein each leg has an exterior side forming part of the exterior of the envelope of the cage and wherein the strap fixed to each of the two segments and extending between the two segments is disposed on the two segments on the exterior side thereof so that the pivot of the corresponding collapsible leg is exterior to the envelope of the cage.

3. The apparatus of claim 1 wherein each of the two segments comprising a collapsible leg is coupled to the end plates by an open hinge.

4. An apparatus for spinal fusions comprising:

two opposing end plates;

at least two opposing collapsible legs disposed between the two opposing end plates, the two opposing end plates and at least two opposing collapsible legs adapted to be arranged and configured into an expanded cage from a collapsed configuration in which the expanded cage assumes a predetermined rigid shape and volume for disposition between two adjacent vertebrae in a disk space therebetween, and in which collapsed configuration the cage is adapted to being posteriorly inserted into the disk space; and locking means for locking the legs and maintaining the cage in an expanded configuration wherein the locking means comprises an over-the-center toggle for each of the at least two opposing collapsible legs, wherein the over-the-center toggle for each of the collapsible legs comprises a resilient strap having two opposing ends, each opposing end of the resilient strap being coupled to one of the two opposing end plates, the strap being coupled to a corresponding collapsible leg so that when the cage is in the expanded configuration, the resilient strap applies a compressive force to the corresponding collapsible leg to maintain the corresponding collapsible leg in a locked configuration.

5. The apparatus of claim 4 wherein the at least two opposing collapsible legs are each comprised of two segments hinged together at or near one end of each segment and hinged to one of the end plates at the opposing end of each segment and wherein each leg has an exterior side forming part of an exterior of an envelope of the cage and wherein the resilient strap is disposed on the two segments on the exterior side thereof.

6. An apparatus for spinal fusions comprising:

two opposing end plates;

at least two opposing collapsible legs disposed between the two opposing end plates, the two opposing end plates and at least two opposing collapsible legs adapted to be arranged and configured into an expanded cage from a collapsed configuration in which the expanded cage assumes a predetermined rigid shape and volume for disposition between two adjacent vertebrae in a disk space therebetween, and in which collapsed configuration the cage is adapted to being posteriorly inserted into the disk space; and an inserter comprised of a tubular member having a distal end and holding clamp disposed on the distal end of the tubular member, the holding clamp adapted to hold the cage in the collapsed configuration for insertion into a confined surgical theater of operation and then on selective activation of a first type by the tubular member configure the cage from the collapsed configuration to the expanded configuration, wherein the inserter comprises a pair of opposing jaws which expand upon the first type of activation of the inserter and which lock the configuration of the cage to assume a predetermined wedge shape to reestablish normal lumbar lordosis.

7. The apparatus of claim 6 wherein on selective activation of a second type by the tubular member the cage is locked into the expanded configuration.

8. The apparatus of claim 7 wherein the inserter comprises a grip, where activation of the first type by the tubular member comprises movement of the grip by a first amount to configure the cage in the expanded configuration and where activation of the second type by the tubular member comprises movement of the grip by a second successive amount to lock the cage in the expanded configuration.

9. The apparatus of claim 6 where the tubular member comprises a hollow tubular housing and a telescopic rod disposed in the hollow tubular housing, the holding clamp being resiliently coupled to the tubular housing, the telescopic rod engaging the holding clamp to manipulate the holding clamp configure the cage from the collapsed configuration to the expanded configuration when the telescopic rod engages the holding clamp.

10. The apparatus of claim 9 where the telescopic rod selectively engages the collapsible legs to configure the legs into a self-locked configuration.

11. A method for performing a posterior interbody spinal fusion comprising:

posteriorly disposing a fusion cage in a collapsed configuration into a disk space between two adjacent vertebrae; and expanding the fusion cage to assume a predetermined rigid shape and volume when disposed between two adjacent vertebrae in a disk space therebetween, by locking three collapsible legs into an expanded configuration between to opposing end plates in which one of the three collapsible legs is medially disposed with respect to the end plates on a first side of the cage and two of the three collapsible legs are laterally disposed with respect to the end plates on a second side of the cage, wherein locking the collapsible legs comprises rotating each of two segments hinged together at or near one end of each segment and hinged to one of the end plates at the opposing end of each segment, wherein rotating each of two segments comprises flexing the hinge coupling the two segments together at or near one end of each segment, wherein flexing the hinge coupling the two segments together comprises flexing a flexible strap fixed to each of the two segments and extending between the two segments.

12. The method of claim 11 wherein flexing a flexible strap fixed to each of the two segments comprises pivoting the two segments about the flexible strap about an axis disposed exteriorly to the envelope of the cage.

13. The method of claim 11 wherein rotating each of two segments comprises rotating the two segments of the collapsible leg about corresponding open hinges defined in the end plates.

14. A method for performing a posterior interbody spinal fusion comprising:

posteriorly disposing a fusion cage in a collapsed configuration into a disk space between two adjacent vertebrae; and expanding the fusion cage to assume a predetermined rigid shape and volume when disposed between two adjacent vertebrae in a disk space therebetween, by locking three collapsible legs into an expanded configuration between to opposing end plates in which one of the three collapsible legs is medially disposed with respect to the end plates on a first side of the cage and two of the three collapsible legs are laterally with respect to the end plates on a second side of the cage, where locking three collapsible legs into an expanded configuration comprises actuating an over-the-center toggle for each of the collapsible legs wherein actuating an over-the-center toggle comprises stretching a resilient strap having two opposing ends, each opposing end of the resilient strap being coupled to one of the two opposing end plates, the strap being coupled to a corresponding collapsible leg so that when the cage is in the expanded configuration, the stretched resilient strap applies a compressive force to the corresponding collapsible leg to maintain the corresponding collapsible leg in a locked configuration, any movement of the collapsible leg out of the locked configuration tending to further stretch the resilient strap.

15. The method of claim 14 wherein the at least two opposing collapsible legs are each comprised of two segments hinged together at or near one end of each segment to define an outwardly extending pivot point, and wherein each segment is hinged to one of the end plates at the opposing end of each segment and wherein each leg has an exterior side forming part of an exterior of an envelope of the cage and wherein the resilient strap is disposed on the two segments on the exterior side thereof, wherein moving the collapsible leg out of the locked configuration rotates the segments about the exterior pivot point causing further stretching of the resilient strap.

16. A method for performing a posterior interbody spinal fusion comprising:

posteriorly disposing a fusion cage in a collapsed configuration into a disk space-between two adjacent vertebrae; and expanding the fusion cage to assume a predetermined rigid shape and volume when disposed between two adjacent vertebrae in a disk space therebetween, by locking three collapsible legs into an expanded configuration between to opposing end plates in which one of the three collapsible legs is medially disposed with respect to the end plates on a first side of the cage and two of the three collapsible legs are laterally disposed with respect to the end plates on a second side of the cage, wherein expanding the fusion cage comprises:
using an inserter comprised of a tubular member having a distal end and holding clamp disposed on the distal end of the tubular member, the holding clamp adapted to hold the cage in the collapsed configuration for insertion into a confined surgical theater of operation,
selectively activating the tubular member to configure the cage from the collapsed configuration to the expanded configuration by using a pair of opposing jaws of the inserter to expand the intervertebral space and to expand the cage, and
locking the configuration of the cage to assume a predetermined wedge shape to reestablish normal lumbar lordosis.

17. The method of claim 16 wherein selectively activating the tubular member also at least temporarily locks the fusion cage into the expanded configuration.

18. The method of claim 17 wherein the inserter comprises a grip, where selectively activating the tubular member the tubular member comprises moving the grip by a first amount to configure the cage in the expanded configuration and then moving the grip by a second successive amount to lock the cage in the expanded configuration.

19. The method of claim 18 where the tubular member comprises a hollow tubular housing and a telescopic rod disposed in the hollow tubular housing, the holding clamp being resiliently coupled to the tubular housing, and wherein moving the grip by a first amount causes the telescopic rod to engage the holding clamp to manipulate the holding clamp configure the cage from the collapsed configuration to the expanded configuration when the telescopic rod engages the holding clamp.

20. The method of 19 where moving the grip by a second successive amount causes the telescopic rod to selectively engage the collapsible legs to configure the legs into a self-locked configuration.

* * * * *